United States Patent [19]
Hallén

[11] Patent Number: 4,623,217
[45] Date of Patent: Nov. 18, 1986

[54] OPTICAL-FIBER LIGHTING UNIT HAVING A MOVABLE LAMP HOLDER

[76] Inventor: Jan-Åke Hallén, Brinketorpsvägen 3, Partille, Sweden, 433 00

[21] Appl. No.: 513,117
[22] PCT Filed: Oct. 18, 1982
[86] PCT No.: PCT/SE82/00337
 § 371 Date: Jun. 15, 1983
 § 102(e) Date: Jun. 15, 1983
[87] PCT Pub. No.: WO83/01372
 PCT Pub. Date: Apr. 28, 1983

[30] Foreign Application Priority Data
Oct. 16, 1981 [SE] Sweden ................. 8106114

[51] Int. Cl.$^4$ .............. G02B 6/00; F21V 7/04
[52] U.S. Cl. .............. 350/96.10; 350/96.18; 362/32
[58] Field of Search ......... 350/96.10, 96.18, 96.20; 362/32; 433/31

[56] References Cited
U.S. PATENT DOCUMENTS

| | | | |
|---|---|---|---|
| 3,758,951 | 9/1973 | Scrivo et al. | 433/31 X |
| 3,805,048 | 4/1974 | Brennesholtz | 350/96.20 X |
| 3,933,409 | 1/1976 | Kloots | 350/96.20 |
| 4,239,331 | 12/1980 | Aoyama | 350/96.20 |
| 4,437,728 | 3/1984 | Ohashi | 350/96.20 |

FOREIGN PATENT DOCUMENTS

| | | | |
|---|---|---|---|
| 0018264 | 10/1980 | European Pat. Off. | 350/96.24 |
| 55-87104 | 7/1980 | Japan | 350/96.20 |

*Primary Examiner*—William L. Sikes
*Assistant Examiner*—Frank Gonzalez
*Attorney, Agent, or Firm*—Holman & Stern

[57] ABSTRACT

Optical-fiber lighting unit, preferably intended for dental work, and comprising a casing (1) wherein there is provided an optical system (12) to which a plurality of optical-fiber conductors (27) are optically connectable via a light switch (26). The light switch (26) comprises an optical device, for example a lens (28), for focusing incident light, and is displaceable along a plane coinciding with an imaginary plane extending through the center axis of the optical-fiber light conductors (27), transversely of the light path from the optical system (12), to a number of positions corresponding at least to the number of end portions of optical-fiber light conductors (27) connectable to the light switch (26), and that the light switch (26) is thereby adapted to focus the light from a light source (11) provided in the optical system (12) to the end portion of at least one optical-fiber light conductor (27).

9 Claims, 8 Drawing Figures

OPTICAL-FIBER LIGHTING UNIT HAVING A MOVABLE LAMP HOLDER

The invention of this application is disclosed in corresponding International Application No. PCTISE 82/00337, filed Oct. 18, 1982.

BACKGROUND OF THE INVENTION

1. Field of the Invention

The present invention relates to an optical-fiber lighting unit, preferably intended for use in dental work, and comprising a casing, in which there is provided an optical system to which a plurality of optical-fiber light conductors are optically switchable via a light switch.

2. Description of the Prior Art

The fiber optics technology is utilized in many different branches and includes the transmission of light through long, thin fibers of glass or other transparent materials. The light is conducted through the fibers in a non-electrical manner by being reflected from wall to wall. No heat is transmitted or generated during this process.

In many types of precision mechanical work it is desirable, and often completely necessary, that a large amount of cold light may be supplied to a work area to enable the work to be performed correctly. Not least for dentists, this is a problem. It is difficult to obtain sufficient light in the oral cavity and at the same time perform work on e.g. a tooth. The dentist himself will often cause, with his body, hand or tool, shadowing of the light provided e.g by adjustable lamps and the like. The teeth are in themselves uneven and are located unevenly in relation to each other which for instance causes that parts of the teeth will be shadowed. Furthermore, it is difficult to get sufficient light for example into bores and at the innerside of the rows of teeth.

Various optical-fiber lighting units are presently commercially available, for example for use in diagnostics but above all for use in dental work. These units are usually made with a space-consuming and heavy apparatus unit in which there are provided a transformer, a fan and a light bulb with a concave mirror. One or several optical-fiber light conductors are connected by means of a coupling to the apparatus unit and are from there extended to one or several hand-held instruments such as hand-mirrors, dental turbines or the like, to which the fiber-optics is connected by means of e.g clips. Mostly, it is necessary to have several light conductors which can be mounted more or less permanently on some of the most frequently used dental tools, as for example a high speed turbine, a low speed electrical motor and a probe. Due to the unwieldy design the unit must be placed comparatively far away from the place of work, so that consequently also the optical-fiber light conductors have to be made long, for instance 2-3 meters. Due to the light losses in the optical-fiber light conductor, which losses may attain a value of 50% per meter, the light bulb used in the unit must admit light of a high intensity and must therefore be a high-power lamp, which at the same time results in the lamp giving off much heat. As an example, in a commercially available unit the light bulb has a power of 150 W. One disadvantage of using such light bulbs are that they are short lived-the manufacture of the optical-fiber lighting unit in question estimates the burning time to be 80-100 hours. Another disadvantage is that the high emission of heat from the unit will inconvenience the dentist as well as the patient. Furthermore, a comparatively large fan must be used for cooling the unit and this fan introduces disturbing noise into the work environment.

In the case where several optical-fiber light conductors, e.g. three, are connected to the same unit, all of them are activated, i.e they give up light, even those that are not used for the time being. Usually the dentist only needs to use one fiber light conductor at the time, e.g. the one mounted on the turbine or the one mounted on a probe, which means that the unit generates unnecessarily much light and heat, since the light bulb of the unit has to be dimensioned so that the light power is sufficient for all three light conductors at the same time.

BRIEF SUMMARY OF THE INVENTION

The object of the present invention is to eliminate the above mentioned drawbacks and to provide an optical-fibre lighting unit capable of a multitude of uses. It is of small size but despite this generates a sufficient amount of light to a place of work via e.g. three different optical-fiber light conductors, each of which is switchable to the light source. The light admitted has to be a non-blinding, white cold light. Due to the small size of the optical-fiber lighting unit it may be mounted close to the place of work whereby the optical-fiber light conductors may be made shorter than what would normally be the case, which decreases the light losses in the optical-fiber light conductors and allows a smaller power of the light bulb to obtain a sufficient intensity of light at the place of work. Further objects are that the unit shall be simple to use, generate the least possible heat, and that the light bulb shall have a long burning time. This is attained in that the light switch comprises an optical means, e.g. a lens, for focusing incident light, said optical means being displacable along a plane coinciding with a plane extending through the center axes of the optical-fiber light conductors, transversely of the light path from the optical system, to a number of positions corresponding at least to the number of end portions of optical-fibre light conductors connectable to the light switch, the light switch thereby being adapted to focus the light from the light source provided in the optical system to the end portion of at least one optical-fiber light conductor.

BRIEF DESCRIPTION OF THE DRAWINGS

One embodiment of the invention will now be described in detail with reference to the accompaning drawings wherein.

DETAILED DESCRIPTION

Figure 1:
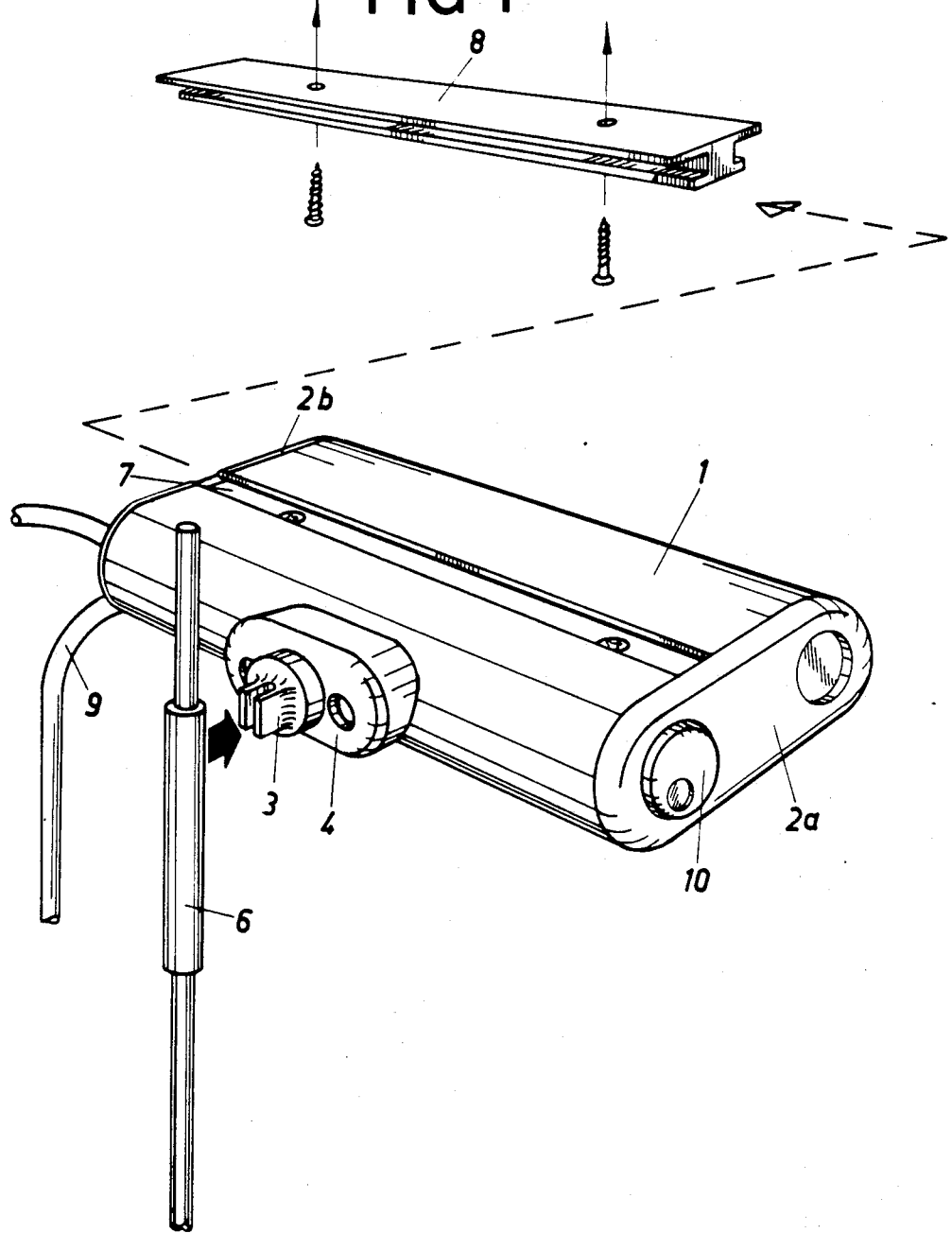
FIG. 1 is a perspective view of an optical-fiber lighting unit according to the invention.

FIG. 1 is a view of an optical-fiber lighting unit according to the invention and intended mainly for dentists but also for other professions with similar demands on lighting units. The optical-fiber lighting unit consists of an injection-moulded casing 1 of aluminum with plastic end walls 2a, 2b. At one of the longer sides, an instrument holder 3 is rotatably mounted on a base plate 4 for a lampholder 5. Various standard tools, such as e.g. a diagnostic probe 6 provided with optical-fibre lighting may be hung onto the instrument holder 3. A rail 8 fits into a slot 7 provided on one of the broad sides of the optical-fibre lighting unit. By means of the rail 8 the unit may be conveniently and detachably mounted on a stand or a work bench near the place of work. Instead of the rail 8 it would of course be possible to use magnets (not shown) for simple mounting of the optical-fiber lighting unit. Electrical power is supplied to the optical-fiber lighting unit via a cable 9 at a potential of e.g. 6 volts. Suitable light intensity for each type of work may be adjusted by means of a potentiometer wheel 10.

Figure 2:
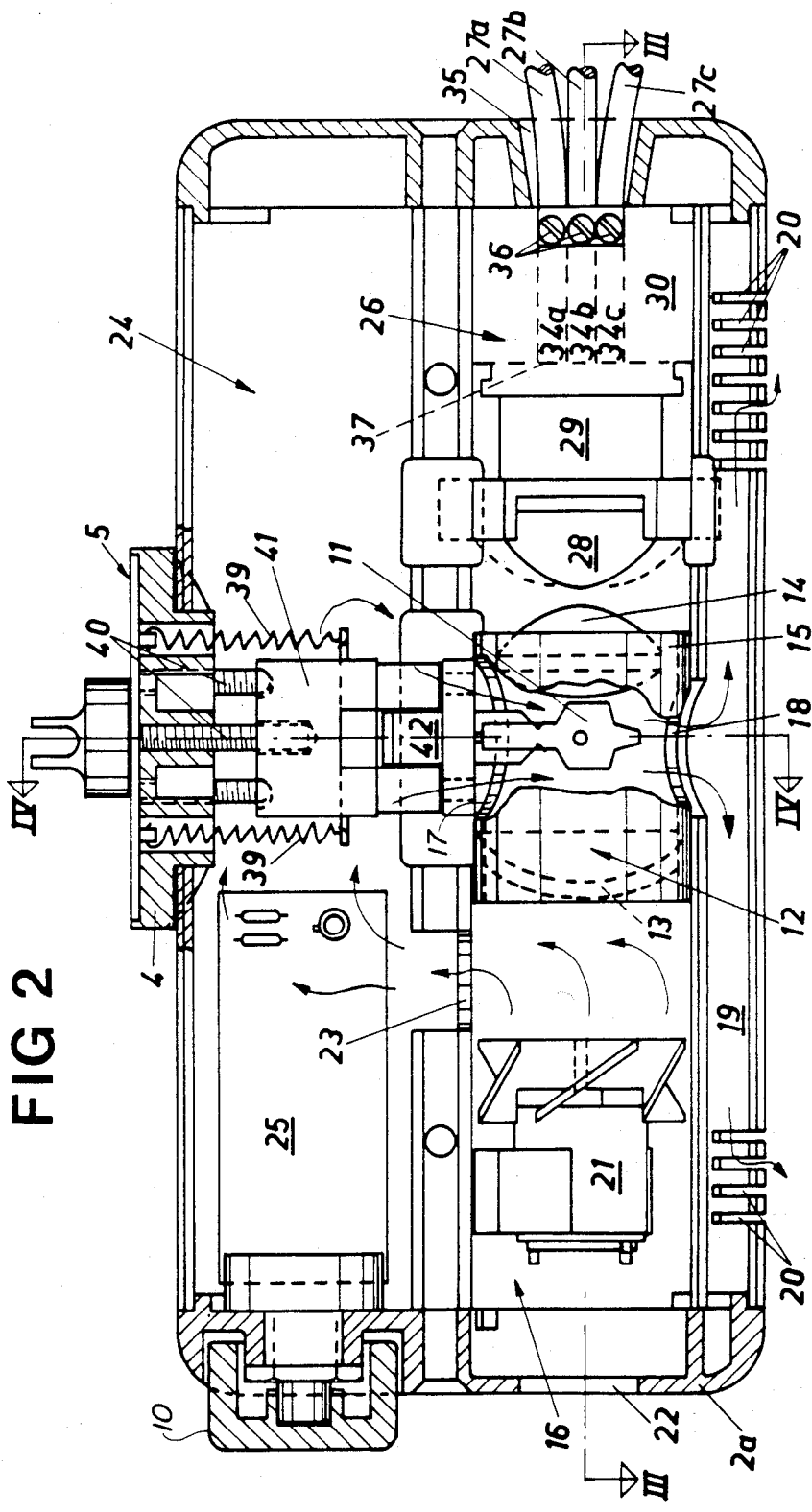
FIG. 2 is a horizontal cross-sectional view showing the optical-fiber lighting unit of the invention.
Figure 3:
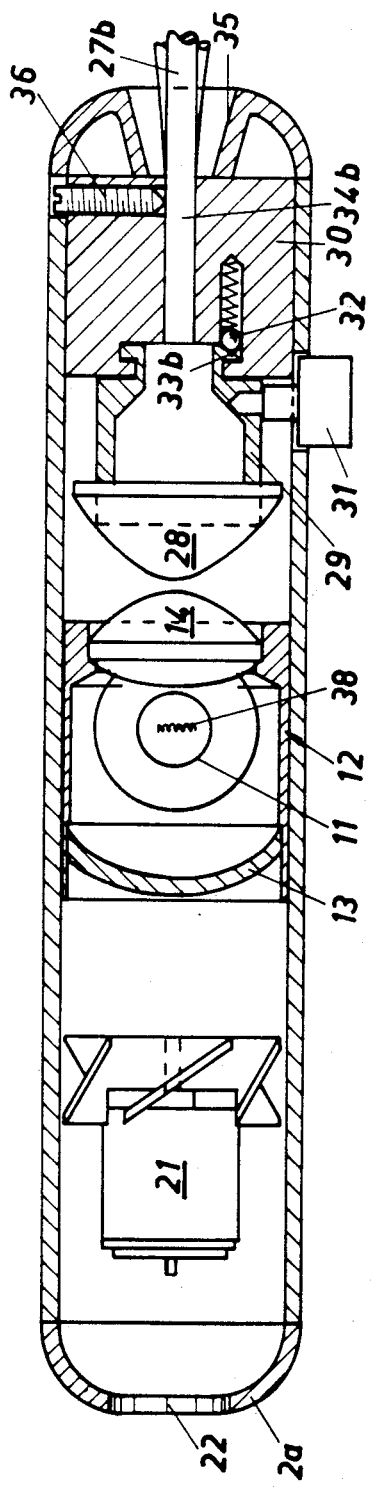
FIG. 3 is a cross-sectional view taken along the line III—III in FIG. 2.
Figure 4:
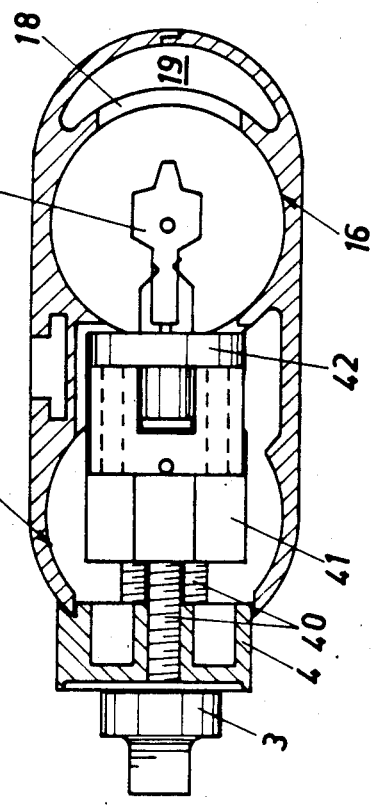
FIG. 4 is a cross-sectional view taken along the line IV—IV in FIG. 2.

FIG. 2 shows a view, partly in section, from the side of the optical-fiber lighting unit with the upper half of the casing removed to illustrate the structure of details within the optical-fiber lighting unit. A halogen lamp 11 with a power of 20 W and mounted in a lamp holder 5 is provided in the center of an optical system 12 comprising a concave mirror 13 and a convex-convex condensor lens 14 secured in a sleeve 15. The sleeve 15 in turn is secured co-axial with a first cylindrical space 16 formed in the casing 1 in such a way, that the halogen lamp 11 may be inserted through a hole 17 in the side of the sleeve 15. A further hole 18 is provided in the opposite side of the sleeve 15 and connects the inner space of the sleeve 15 with a hot air channel 19 provided in the casing 1.

The hot air channel 19 extends along the complete longer side of the optical-fiber lighting unit and permits hot air from the inside of the optical-fiber lighting unit to escape through outlet openings or slots 20 provided in the casing 1. The air is made to flow through the lighting unit by means of a fan 21 provided behind the concave mirror 13 and in the extension of the same cylinder-shaped space 16 wherein the optical system 12 is provided. Air is thereby sucked in through an opening 22 in the front end wall 2a, passes the fan 21 and the rear side of the mirror 13 in through a channel 23 to a second cylindrical space 24 formed in the casing 1, the passing air thereby cooling a circuit card 25 provided with control electronics (not shown in details) for controlling the light intensity of the halogen lamp 11. Further, the air passes past the lamp holder 5 and into the sleeve 15 where the halogen lamp 11, the mirror 13 and the condensor lens 14 will be exposed to cooling air. The air thereafter passes into the hot air channel 19 and out through the slots 20. Due to the low power, 20 W, of the lamp 11 only a slight ventilation is necessary, but despite this, a working life of about 2,000 hours will be obtained for the lamp 11.

In the first cylinder shaped space 16 of the casing 1 there is provided, apart from the fan 21 and the sleeve 15, also a light switch 26, the purpose of which is to focus the light from the halogen lamp 11 to one of the ends of e.g. three possible optical-fiber light conductors 27a, 27b, 27c. Only one at a time of the optical-fiber light conductors 27a–c may transmit light from the optical-fiber lighting unit to an external instrument, i.e. only one conductor can be active whereas the other two are inactive. The light switch 26 mainly consists of a plane-convex lens 28, a metal slide 29, and a holder 30 which is also made of metal, and the light switch is provided in the light path of the optical system 12. The plane-convex lens 28 is secured to the slide 29 which may be actuated manually by means of a control 31 to occupy one of three different positions in the sidewards direction (seen from above). A spring-loaded ball 32 arranged in the holder 30 co-operates with three shallow holes 33a, 33b, 33c provided in one of the guide rails of the slide 29 and assures that the slide 29 will be retained by means of snap action in the position to which it has been adjusted. Three through-bores 34a, 34b, 34c are further provided side by side in the holder 30 and are intended to receive optical-fiber light conductors 27a, 27b, 27c which are pushed in through an opening 35 in the rear end wall 2b. Lock screws 36 are placed transversely of said holes 34 and are adapted to secure the optical-fiber light conductors 27 in place. The ends of the optical-fiber light conductors 27 are disposed in the focal plane 37 of he plane-convex lens 28, whereby maximum light transmission is obtained to that optical-fiber light conductor 27 which at the moment is in the active position.

To obtain the largest possible light transmission, it is very important that the halogen lamp 11 is placed in the center of the optical system 12, i.e. in such a manner, that a sharp image of the glow-wire 38 of the lamp 11 falls directly onto the end of that optical-light conductor 27 which at the moment is adjusted into the active position. For this purpose a base plate 4 is arranged at the middle of one of the long sides of the optical-fiber lighting unit and secured in the casing 1 by means of two screws (not shown). The base plate 4 is mechanically connected with a movably arranged lamp support 41 by means of two tension springs 39 and four adjustment screws 40. A lamp holder 42 of a ceramic material carrying the halogen lamp 11 is inserted into the lamp support 41 which is made from a heat resistant plastic. The two springs 39 are disposed at opposite sides of the lamp support 41 and tend to pull the lamp support 41 closer to the base plate 4. One of the four adjustment screws 40, which are made with semi-spherical ends, is positioned in the center of the lamp support 41 on that side which faces the base plate 4, whereas the other three adjustment screws 40 are positioned symmetrically and peripherally around the central screw in such a manner, that they form the corners of an imaging triangle. Thus, by means of the centrally located screw 40 the halogen lamp 11 may be displaced sideways transversely to the center axis of the optical system 12, and by means of the other three adjustment screws 40 the halogen lamp 11 may be adjusted in an imaginary plane which cuts through, on the one hand, the center axis of the optical system 12 and on the other hand, the glow-wire 38 of the halogen lamp 11.

Figure 5:
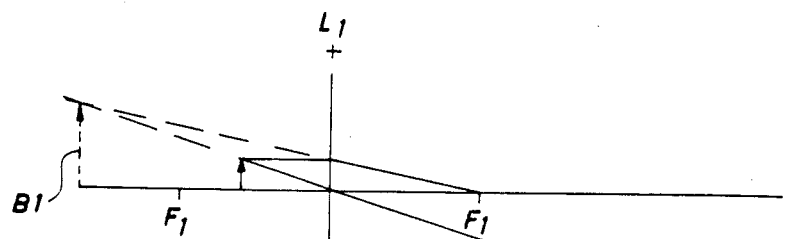
FIGS. 5, 6 and 7 are diagrams which illustrate the theoretical path of light in lens systems.
Figure 6:
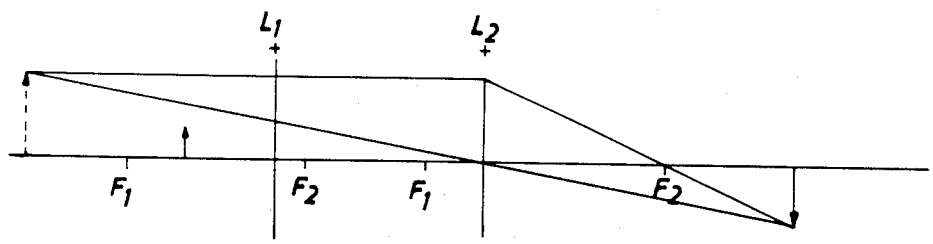
Figure 7:
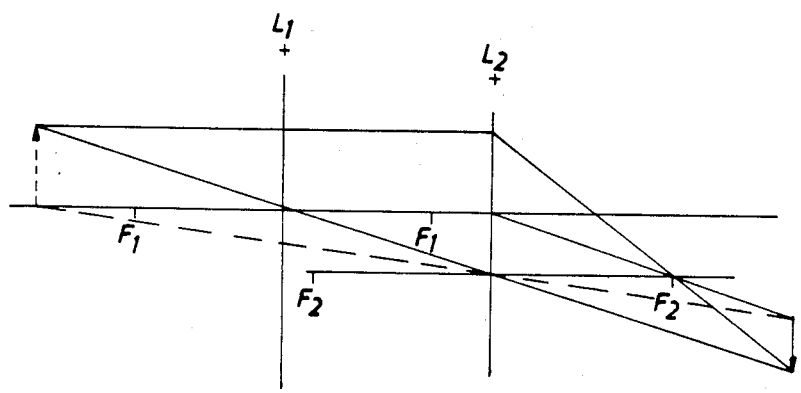

The functioning of the optical system 12 and the light switch 26 is shown more in principle in FIGS. 5, 6 and 7. FIG. 5 illustrates a simple optical system including only one lens L1 the focal point F1 of which is located at a certain distance from the lens. If a light source, e.g. a light bulb provided with a glow-wire (here symbolized by an arrow) is placed between the lens L1 and the focal point F1, behind the lens L1 (i.e. to the left of the lens), a virtual image B1 is obtained behind the lens. With the aid of a further lens L2 placed at a distance in front of the lens 1 (see FIG. 6) this virtual image will be focused on the end surface of an optical-fiber light conductor.

If the second lens L2 is displaced transversely to the light path of the optical system (as illustrated in FIG. 7), the focused image of the glow-wire will consequently also be displaced, and in this way the desired displacement of the light spot to an end surface of another optical-fiber light conductor will be obtained.

Figure 8:
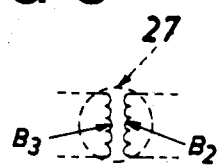
FIG. 8 illustrates diagrammatically the "picture" which is focused on the endportion of an optical-fiber light conductor.

The highest exchange of light from the light source 11 is obtained in that concave mirror 13 and the lens 14 are arranged in relation to the light source 11 in such a way, that the image B3 of the glow-wire reflected by the mirror is focused, mirror-reversed, just adjacent to the "direct image B2" of the glow-wire at the end of the optical-fiber light conductor 27 (see FIG. 8). A substantially spot-shaped or square-shaped light image will thereby be obtained which contributes to the light exchange from the light source 11.

The invention is, of course, not limited to the embodiment described above, but a plurality of alternative embodiments are conceivable within the scope of the appended claims. Thus, instead of displacing the slide 29 with the plane-convex lens 28 with respect to the holder 30 and the sleeve 15 with the optical system 12, it is conceivable to arrange the sleeve 15 and the plane-convex lens 28 as an integrated system and to displace the whole of this in relation to the holder 30 with the optical-fiber light conductors 27.

It is also conceivable, instead of a single optical-fiber light conductor 27 per inlet (hole 34), to arrange two or several per inlet, e.g. by pressing the ends of two optical-fiber light conductors 27 against each other so that each conductor 27 will take the shape of the surface of half a circle. In this way two or several conductors 27 may be illuminated simultaneously, although the light switch 26 is in a single position only.

I claim:

1. In an optical-fiber lighting unit including a casing having an optical system therein with a light source to which a plurality of optical-fiber light conductors are optically connectable, the end faces of the light conductors being aligned in an alignment line transverse to their optical axes, the improvement comprising:
    a lens mounting means slidably mounted within the casing for displacement along a path parallel to the alignment line of the end faces of the light conductors to a number of positions corresponding to the end faces of the light conductors; and
    a focusing switch lens mounted in said mounting means, said switch lens being adapted to focus light from the light source onto the end face of a respective light conductor, so that the light can be supplied to at least one light conductor at a given time via said switch lens.

2. An optical-figer lighting unit as claimed in claim 1 wherein:
    said light source comprises a glow wire;
    a mirror is provided on one side of said glow wire; and
    a lens is arranged at the opposite side of said glow wire so that the image of the glow wire reflected by said mirror is focused mirror-reversed adjacent the direct image of the glow wire at the end of the optical-fiber light conductor and a substantially spot-shaped light image is obtained.

3. An optical-fiber lighting unit as claimed in claim 1 wherein:
    said lens mounting means comprises a slide arranged in the light path in front of a holder mounted in the casing which receives the end portions of the light conductors.

4. An optical-fiber lighting unit as claimed in claim 2 wherein:
    said lens mounting means comprises a slide arranged in the light path in front of a holder mounted in the casing which receives the end portions of the light conductors.

5. An optical-fiber lighting unit as claimed in claim 1 wherein the light source comprises:
    a lamp holder;
    means for movably mounting said lamp holder in the casing for displacement in a longitudinal direction transverse to the light path of the optical system; and
    angular adjusting means for angularly adjusting said lamp holder relative to a center axis extending in said longitudinal direction transverse to the light path of the optical system.

6. An optical-fiber lighting unit as claimed in claim 5 wherein:
    said light source further comprises a base plate mounted on the casing;
    said means for movably mounting said lamp holder comprises a central adjustment screw rotatably mounted in said base plate and engaging said lamp holder; and
    said angular adjusting means comprises a plurality of adjusting screws rotatably mounted in said base plate and engaging said lamp holder in spaced relationship around said central adjustment screw, and a plurality of tension springs operatively connected between said base plate and lamp holder for urging said lamp holder into engagement with said screws.

7. An optical-fiber lighting unit as claimed in claim 1 wherein:
    the casing comprises two profiled interconnectable casing halves which in their interconnected condition form two cylindrical spaces separated from one another;
    ventilating air inlet and slotted exit openings are provided through said casing; and
    openings are provided between said spaces for interconnecting said spaces so that ventilating air may pass between the spaces and pass arond the light source and said optical system before it leaves the casing through said exit slots in said casing.

8. An optical-fiber lighting unit as claimed in claim 6 wherein:
    the casing comprises profiled interconnectable casing halves which in their interconnected condition form two cylindrical spaces separated from one another;
    ventilating air inlet and slotted exit openings are provided through said casing; and
    openings are provided between said spaces for interconnecting said spaces so that ventilating air may pass between the spaces and pass around the light source, said lamp holder and said optical system before it leaves the casing through said exit slots in said casing.

9. An optical-fiber lighting unit as claimed in claim 8 and further comprising:
    a blower fan mounted within one of said casing halves adjacent said ventilating air inlet for forcing ventilating air through said casing.

* * * * *